United States Patent [19]

Prestele et al.

[11] 4,395,259

[45] Jul. 26, 1983

[54] DEVICE FOR THE INFUSION OF FLUIDS INTO THE HUMAN OR ANIMAL BODY

[75] Inventors: Karl Prestele, Erlangen; Manfred Franetzki, Uttenreuth; Erich Reif, Erlangen, all of Fed. Rep. of Germany

[73] Assignee: Siemens Aktiengesellschaft, Berlin & Munich, Fed. Rep. of Germany

[21] Appl. No.: 301,780

[22] Filed: Sep. 14, 1981

[30] Foreign Application Priority Data

Sep. 22, 1980 [DE] Fed. Rep. of Germany ....... 3035670

[51] Int. Cl.$^3$ .......................................... A61M 37/00
[52] U.S. Cl. .............................. 604/67; 128/DIG. 13
[58] Field of Search ............... 128/214 E, 214 F, 260, 128/DIG. 12, 213, 903, 419 P, DIG. 13; 604/891; 340/502, 504, 825.69, 825.72

[56] References Cited

U.S. PATENT DOCUMENTS

| 3,837,339 | 9/1974 | Aisenberg et al. | 128/903 |
| 4,077,405 | 3/1978 | Haerten et al. | 128/214 F |
| 4,137,913 | 2/1979 | Georgi | 128/214 F |
| 4,146,029 | 3/1979 | Ellinwood | 128/260 |
| 4,146,029 | 3/1979 | Ellinwood | 128/260 |
| 4,232,679 | 11/1980 | Schulman | 128/419 PG |
| 4,265,241 | 5/1981 | Portner et al. | 128/260 |
| 4,281,664 | 8/1981 | Duggan | 128/903 |
| 4,308,866 | 1/1982 | Jelliffe et al. | 128/214 E |

FOREIGN PATENT DOCUMENTS

2920976 of 0000 Fed. Rep. of Germany .

OTHER PUBLICATIONS

Schubert et al., "An Implantable Artificial Pancreas", Medical and Biological Engineering and Computing, (Jul. 1980), pp. 527–537.

Primary Examiner—Richard J. Apley
Assistant Examiner—George Yanulis
Attorney, Agent, or Firm—Hill, Van Santen, Steadman, Chiara & Simpson

[57] ABSTRACT

An exemplary embodiment comprises a metering device which can be worn on the body or which is preferably implantable in the body, the metering device exhibiting a delivery unit for the dosed delivery of the fluid from a supply container to a discharge aperture of a catheter and also exhibiting an appertaining operating circuit, and an external control and programming device. The operating circuit in the metering device and the control circuit in the control device can be inductively coupled for operational signal transmission, to which end at least one transmission coil is present in the control device and at least one reception coil is present in the metering device. Given implanted devices, it is the object of the disclosure to guarantee the highest degree of patient security. For function monitoring of operating parameters of the metering device the metering device exhibits a transmitter whose signals can be received in a receiver outside of the patient's body and, under certain conditions, can be evaluated. In addition to pure function monitoring, an acknowledgement of signals as well as an answerback of the value of one or more operating parameters is possible.

28 Claims, 6 Drawing Figures

DEVICE FOR THE INFUSION OF FLUIDS INTO THE HUMAN OR ANIMAL BODY

BACKGROUND OF THE INVENTION

The invention relates to a device for the infusion of fluids into the human or animal body, comprised of a metering device which can be carried on the body or, preferably, can be implanted in the body, said metering device exhibiting a delivery unit for the dosed delivery of the fluid from a supply container to the discharge aperture of a catheter and further exhibiting an appertaining operating circuit, and an external control and/or programming device, wherein the operating circuit in the metering device and the control circuit in the control device can be inductively coupled for the purpose of operational signal transmission, to which end at least one transmission coil is provided in the control device and at least one reception coil is provided in the metering device.

Such a device is meant to be employable, in particular, for insulin infusion for diabetes therapy as a so-called "artificial pancreas".

A device of the type initially described is known from the U.S. Pat. No. 4,077,405 in which an external control and/or programming device is alloted to an implantable device housing with the delivery and metering unit. The control device is constructed as a program generator for an on-off valve in the metering device, such control device containing, in detail, a control signal generator, a program memory, a program input unit for inputting a time or switching frequency program, as well as an information generator for displaying, for example, the prorgram state, the time of day or other information. Beyond that, an implantable infusion device is known in which the delivery and metering unit is specifically formed by means of a roller pump which is controlled by means of a stepping motor. In such a case, it is already provided to monitor the running of the roller pump in that a magnet is assigned to each pump roller which periodically closes a reed contact when the pump is running and generates a signal. These monitoring signals essentially serve for readjusting the roller pump in the operating circuit of the implanted device. Thus, a back-coupling of the function of the delivery and metering unit to the operating circuit is provided in the implanted device in the prior art.

SUMMARY OF THE INVENTION

The object of the invention is to improve infusion devices of the prior art in such manner that a function check is assured at any time even given a metering device implanted in the human body. In addition to monitoring the function of the metering device, a transmission of infusion programs which are deposited in memories assigned to the operating circuit should also be capable of being checked.

This object is inventively achieved in that means for function monitoring of operating parameters of the metering device exist, to which end at least the metering device exhibits a transmitter whose signals can be received in a receiver outside of the patient body and, if need be, can be evaluated.

A complete function monitoring of the body-internal and body-external device units is possible with the invention. The purely operational function of the delivery and metering unit can be covered by means of a separate monitoring device. When a roller pump with stepping motor drive is employed as the delivery unit, then a magnetic scatter field is generated when the stepping motor is driven and said magnetic scatter field can be received as a signal in the separate monitoring device. Each motor step can then be converted into an acoustical and/or optical signal. The stepping motor frequency can be measured with an additional frequency meter and the infusion rate, for example, can be directly determined therefrom, said infusion rate being directly displayable in insulin units per hour (IU/h) at a display unit at the monitoring device, specifically for insulin infusion, after calibration.

Given inventive devices without stepping motor drive, an additional induction coil as a separate transmitter is provided in the metering device.

In a further development, the control or, respectively, programming operation of the metering device can also be monitored with such an inventive device. If, for example, the external control device exhibits an encoder and the operating circuit in the metering device exhibits a decoder, so that the control and/or programming signals are transmitted encoded from the control device to the implanted decoding device and are there decoded for further processing, then the stepping motor or, respectively, transmitter in the implanted dosing device can be directly driven by the decoder, so that an output signal is generated after reception of a control and/or programming signal. Input signal and output signal of the operating circuit, thus, are chronologically correlated to one another, which can be verified by means of checking the chronological coincidence of the signals. Thus, the possibility of acknowledging control and/or programming signals is given.

In an additional inventive development, the acknowledgement signal can also be employed for the answer back of one or more device-internal parameters. Whereas, given a pure acknowledgement with a coincidence circuit, the only thing which is registered is whether, after redrive, or, respectively, reprogramming in the external control device, a signal generated by the stepping motor or, respectively, transmitter in the implanted metering device arrives within a specific interval of expectation, in this development of the invention a specific time delay of the acknowledgement signal is employed for further information transmission. To that end, measured value generators for generating electrical signals corresponding to the operating parameters and signal/time transducers which serve as controllable delay elements must be present in the implanted metering device.

Specific operating parameters for the answer back can, for example, be the internal pressure in the metering device, which represents a measure for the degree of filling of the supply container, or can also be the pressure in the delivery system. Particularly in the latter case, the possibility is specifically given of monitoring the delivery system as to flow obstacles or blockages and to initiate appropriate counter-measures when specific limit values of the pressure are reached. In addition, the operating parameters to be answered back can, for example, also be the insulin dose added up since the last programming operation or continuously added up by means of summation of the control pulses in a counter.

In order to realize the answer back, the measured value of the signal transducer influences the transmission signals generated in the metering device via a time delay element for each respective operating parameter. In the external control and/or programming device, the signals of the metering device are detected in correlation to the control or, respectively, programming pulse and the chronological delay between the signals is evaluated as information. Thereby, the information processing can be simplified in that only the transgression of the prescribed limit values is detected. In order to measure the operating parameters encoded as time intervals, analog or digital chronometry methods can be applied in the external control device. It is thereby particularly simple when the timer is comprised of a counter post-connected to a clock generator, whereby the clock generator or counter is started by the control and/or programming signal and the counter reading at the arrival of the respective answer back signals is output. This can ensue by means of intermediate storage and/or display.

In addition to the monitoring, acknowledgement and answer back function, it is now also possible with the invention to directly drive the delivery unit, given metering devices which are programmable per se, by bypassing the operating circuit with memory units. Since one or more motor steps are triggered after each programming signal, the stepping motor can be directly driven from the outside with a desired frequency by means of an appropriately frequent repetition of programming signals. In this case, the programming signals are expediently selected in such manner that the program memories in the metering device are respectively set to zero so that no interference from the external control and internal control can occur due to the operating circuit.

Further details and advantages of the invention derive from the following figure description of exemplary embodiments on the basis of the accompanying drawing sheets in conjunction with the further subclaims; and other objects, features and advantages will be apparent from this detailed disclosure and from the appended claims.

DETAILED DESCRIPTION

In the figures, identical parts are provided with the same reference characters.

Figure 1:
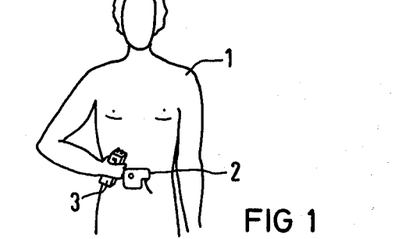
FIG. 1 shows a patient with an implanted metering device and an external control and programming device.

FIG. 1 shows a patient 1 in whom a metering device 2 is implanted. The implantation is formed of a flat capsule located under the skin with a fluid discharge which is placed in muscle or, respectively, fatty tissue. A control or, respectively, programming device 3 can be externally placed at the level of the implanted metering device 2 by the patient 1 or, respectively, by the physician. By means of inductive signal transmission, the operating circuit in the implanted metering device can be activated for the changeover of the infusion rate or, respectively, for the acceptance of an infusion program. To that end, the operating circuit in the metering device 2 exhibits corresponding memory units which, in the simplest case, can comprise a first counter for the determination of a basal infusion rate and of a second counter for the determination of a chronologically limited (relatively short duration) auxiliary infusion rate. However, memories with larger memory capacity, for example, so-called RAM's (random access memories) or so-called FIFO's (first-in, first out memory stacks) can also be employed. Either a daily program or a brief porgram of the infusion course is read into such semiconductor memories with a single programming operation by means of appropriately encoded pulse salvos. Such stored infusion programs are worked off either cyclicably or on a one-time basis with the assistance of the operating circuit in a corresponding time correlation.

Figures 2, 3:
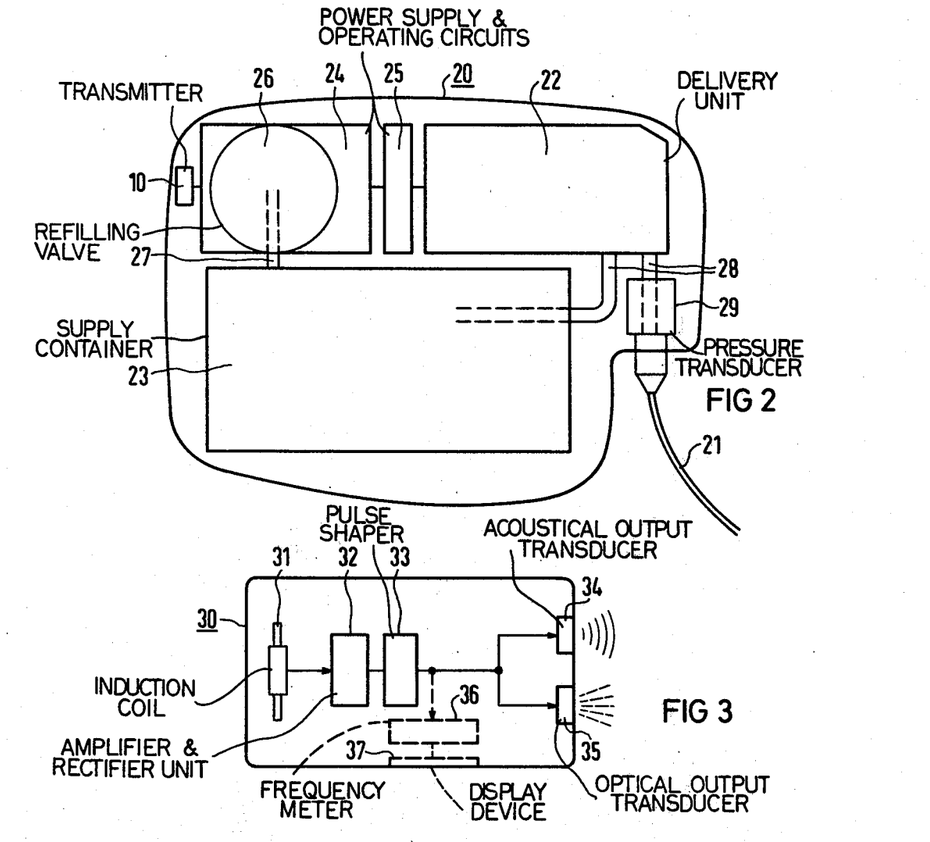
FIG. 2 shows the structure of the implanted metering device.
FIG. 3 shows the structure of a separate monitoring device.

In FIG. 2, 20 indicates the housing capsule of the metering device 2 according to FIG. 1. This is expediently designed in a flat shape similar to that of a heart pacemaker and is made of a body-tolerated material, for example, of titanium. The inside of the housing is hermetically sealed; a discharge catheter 21 leads from the housing discharge into, for example, a body vein. A delivery unit 22 is situated in the inside of the capsule, metered infusion fluid being delivered by said delivery unit 22 from a supply container 23 to the discharge opening of the catheter 21. Reference numerals 24 and 25 indicate units which contain the aforementioned operating circuit with memory units as well as a battery for the electrical power supply. A refilling valve 26 has a self-sealing closure through which fluid can be refilled percutaneously into the implanted metering device by means of a hypodermic or the like. The fluid passes from the refilling valve 26 into the supply container 23 via a connection line 27 and moves from there to the connection of the discharge catheter 21 via a further connection line 28 which is coupled with the delivery and metering unit 22.

Further, 29 indicates a pressure signal generator which is situated between the delivery unit 22 and the connection of the discharge catheter 21. A roller pump, for example, is employed as the delivery unit 22. Then, the line 28 can directly form the delivery tube of the roller pump which leads from the supply container 23 up to the connection of the catheter 21. In this case, the pressure signal generator 29 is disposed at the terminating part of the delivery tube of the roller pump 22. Its function shall be described further below.

As already indicated, the operating circuit with the control and memory units within the capsule 20 of the metering device 2 is activated by the external control and programming device 3 by means of inductive signal transmission. To that end, the external control circuit exhibits a transmitter for generating a magnetic alternating field and the internal control circuit exhibits an inductive receiver. In order to exclude spurious transmissions, the signals are transmitted encoded. To that end, the external control and programming device 3 contains an encoder and the internal metering device contains a decoder. The decoder decodes the signals received as pulse salvos in accord with the prescribed code. Given operational control of the metering device by the external device, a decoded signal directly activates the driver of the delivery unit. Given program tramsmissions, an entire infusion program, in contrast thereto, is transmitted encoded as a pulse salvo, is decoded by the decoder, and is correspondingly deposited into the memory of the metering device. In this case, the motor driver is activated in accord with the deposited program.

When a roller pump is employed as the delivery unit 22, being driven by a stepping motor, then a magnetic scatter field is generated when the stepping motor is driven. Up to a certain distance (approximately 0.15 m), this magnetic field can be detected by an induction coil with a following amplifier and can be displayed by means of optical and/or acoustical signals. Thus, a monitoring of the metering device 2 can already be realized by means of the reception of this magnetic scatter field. Alternatively, a special transmitter can be present in the capsule 20 of the metering device 2. Such a transmitter can generate either individual pulses or signals with a specific carrier frequency; in the latter case, the input circuit of the external receiver is also tuned to the carrier frequency. In this manner, a greater range and/or insensitivity to disruption of the transmission can be achieved.

In FIG. 3, 30 indicates the housing of a separate monitoring device. Situated in the housing 30 are an induction coil 31 as the reception coil which is followed by an amplifier and rectifier unit 32, as well as a pulse shaper 33. An acoustical display unit 34 on the one hand and an optical display unit 35 on the other hand are activated by the pulse shaper 33. Each received signal, for example, each pulse of the device-internal stepping motor, can be displayed and, particularly, can be listened to. Thereby, given a nonselective amplifier 32, it is not only the signals of the implanted operating circuit which can be monitored but, rather, the signals of the external control and programming device 3 as well. Further, a frequency meter 36 can be connected behind the pulse shaper 33. The frequency of the received signals which, for example, corresponds to the stepping motor frequency and thus, is proportional to the current delivery rate of the metering device is measured by the frequency meter 36. This frequency can be displayed at a display device 37 with digital display. The display unit 37 can be calibrated directly in units of the delivery rate such as, for example, insulin units per hour (IU/h).

Figure 4:
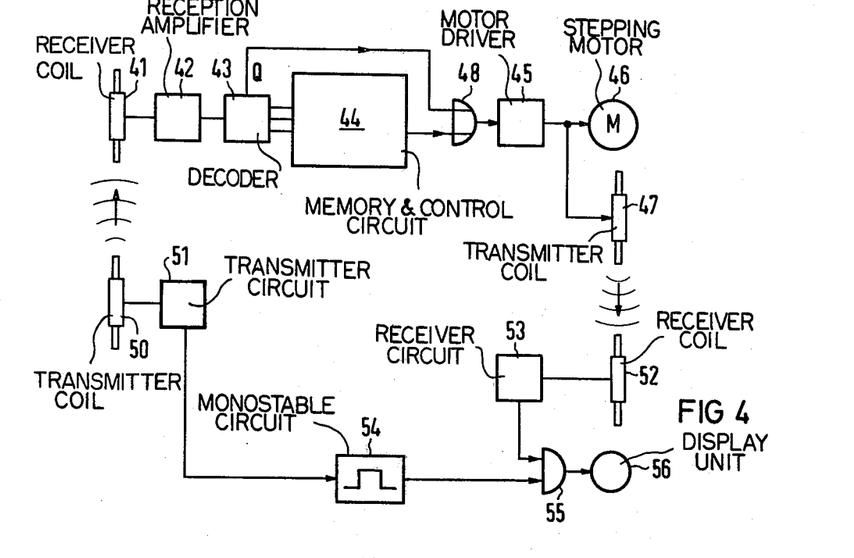
FIG. 4 is a block diagram of the implanted operating circuit showing its active connection with the external circuit for the purpose of acknowledging control and/or programming signals.

In FIG. 4, 41 indicates a receiver coil in the implanted metering device 2. A decoder 43 is driven by the receiver coil 41 via a reception amplifier 42, said decoder 43 being followed, as a significant part of the operating circuit of the metering device 2, by a memory and control circuit 44. The latter controls the motor driver 45 of a stepping motor 46 for the delivery unit. Thus, this corresponds to the previously known operating circuit of the implanted metering device. Inventively, an additional output signal is generated by the decoder 43 at each decoding of a pulse salvo received by the receiver coil 41 according to a prescribed code, said additional output signal directly activating the motor driver via a logical OR element 48 while bypassing the memory and control circuit 44.

Given metering devices without a stepping motor or, respectively, in order to achieve a greater range and/or greater protection against disruption, a separate induction coil 47 can be directly activated, facultatively, or can be activated with a preconnected oscillator in order to generate a carrier frequency. In this manner, one likewise obtains magnetic signals which can be received by a receiver, for example, according to FIG. 3, situated outside of the patient's body.

Thus, it is guaranteed by means of the above circuit of FIG. 4 that an output signal is generated in the metering device 2 at each signal transmission from the external control and programming device 3 to the metering device 2. Thereby, the signal transmission can apply on the occasion of the control or, respectively, further control of the metering device 2 but can also be valid upon occasion of the transmission of an entire infusion program. However, output signals are also generated in the metering device 2 when the motor driver 45 is driven in accord with a prescribed time correlation when working off the infusion program deposited in the memory units.

In order to acknowledge the control and programming signals, the external control and programming device 3 is completed with means for the coincidence measurement of the signals. The control circuit generally exhibits a transmission coil 50 which is driven by a transmitter 51. In addition, a reception coil 52 is present which drives a receiver 53. For the purpose of coincidence comparison, the last signal of the transmission salvo triggers a monostable circuit (monoflap) 54 with a prescribed pulse time. The outputs of the monostable circuit 54 and of the receiver 53 are linked via a logical AND element 55 which drives a display unit 56. A display and, thus, the acknowledgement of the transmission signal only ensues at the signal generator (i.e. display unit or acoustical or optical transducer unit) 56 when a reception signal has been detected after the transmission signal in the time interval prescribed by the monostable circuit 54. When no acknowledgement signal is received in the prescribed time interval, then the programming operation must be repeated with a reduced distance between the programming device 3 and the metering device 2.

Figure 5:
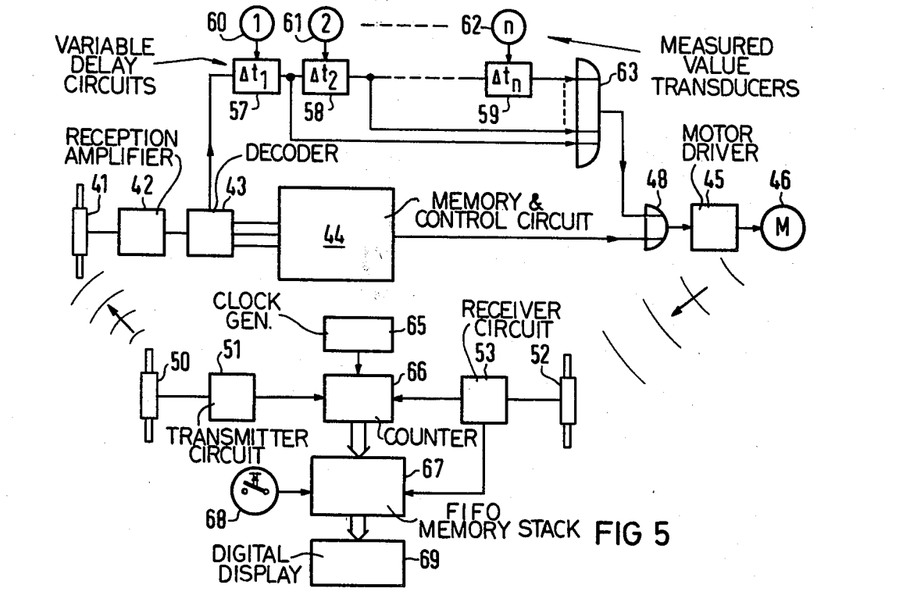
FIG. 5 shows the structure of a circuit corresponding to FIG. 4 for the answer back of n operating parameters of the metering device.

In FIG. 5, reference numerals 41 through 46, 48, as well as 50 through 53 designate the same units as in FIG. 4. Individually controllable delay elements 57 through 59 are connected in series in the bypass line for bypassing the operating circuit 44 which includes the control and memory unit. Each delay element 57 through 59 is driven by one of the measured value generators such as 60 through 62. The electrical signal of the respective measured value generator is determined by the value of a physical or electrical operating parameter. For example, a first measured value generator (e.g. 60) is a pressure/resistance transducer with which the internal pressure of the housing, which can be a measure for the state of filling of the supply container 22, is determined. The pressure in the delivery system itself can be identified with a second measured value generator (e.g. 61), whereby flow impedances as well as blockages in the thin-luminal tubes can be identified. Finally, with a third measured value generator (e.g. associated with a third input to OR circuit 63), the infusion dose added up since the last programming operation or the infusion dose continuously added up by means of summation of the control pulses in a counter can be employed as a control magnitude for a delay element. Further measured value generators for other device parameters are conceivable. In FIG. 5, n individual measured value generators with a respective, appertaining delay element are illustrated.

The outputs of the n individual delay elements such as 57 through 59 are logically linked via an OR circuit 63 with n inputs. The output of OR circuit 63 in turn leads via the OR circuit 48 and motor driver 45 to the motor coil 46. Pulses of a specific time duration $\Delta t_i (i=1$ through n) corresponding to the measured values of the parameters to be monitored are thus generated with the delay elements such as 57 through 59 which may take the form of monostable circuits with controllable time duration. The respective falling edge of a pulse from each monostable (such as 57) triggers the following monostable circuit (such as 58). The motor drive 45 and the motor coil 46 are simultaneously activated via the OR elements 63 and 48.

In this case, the timer in the external control device is realized as a counter 66 driven by a clock generator 65. At the respective termination of a programming salvo, the counter 66 is reset by the transmitter 51 and is subsequently started for counting the pulses. At each respective detection of an answer back signal transmitted by the metering device, the counter 66 is stopped by the receiver 53 and the respective counter reading is deposited in a FIFO 67. Subsequently, the counter 66 is again reset. A suitable sequence control is present for recording the counter reading and for the subsequent resetting.

Upon transmission of a plurality of operating parameters, thus, the counter readings of the counter 66 can be successively stored in the FIFO 67 as information. Accordingly, the readout ensues successively, this being possible by means of polling with a manually actuatable keyer 68. The measured values are displayed at a digital display unit 69 which if need be, is calibrated for the operating parameters.

In FIG. 6, 41 through 46 and 48 as well as 50 through 53 again indicate the units described above. The motor driver 45 is again driven by the decoder 43 given bypass of the memory and control circuit 44. A monostable circuit 70 is specifically inserted in the control line and is actuated to its nonstable condition by the output signal of the decoder 43. In order to set the delay time, the time-determining resistor of the monostable circuit 70 is designed as a variable resistor of a pressure/resistance transducer 71. Proportional to the value of the resistor, thus, the motor driver 45 is activated with a chronological delay via the control line and the answer back signal is transmitted with particular chronological spacing.

Figure 6:
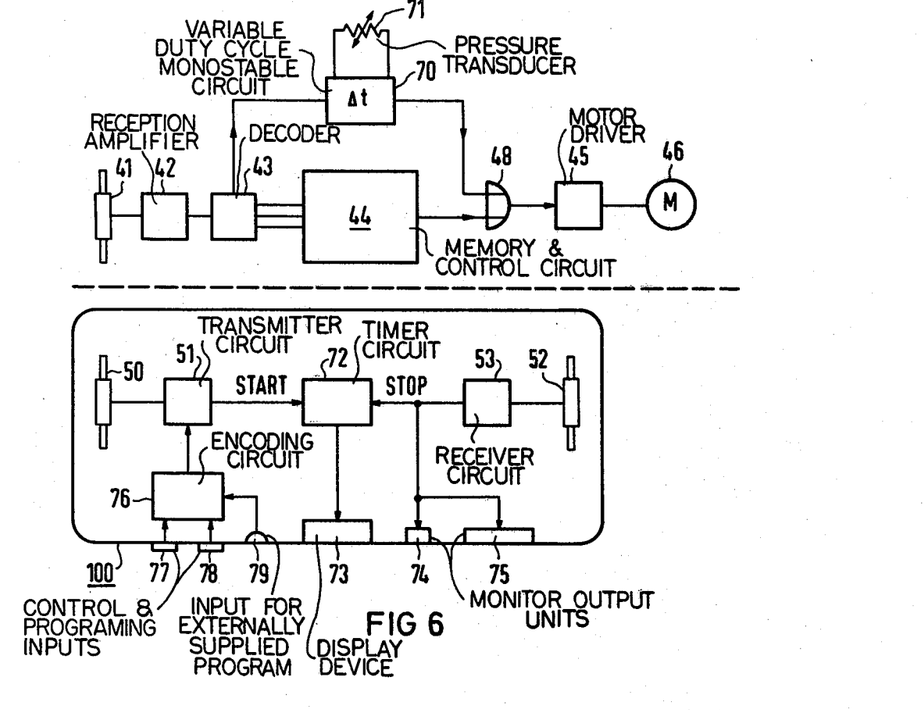
FIG. 6 shows the structure of a circuit corresponding to FIG. 5 for the answer back of a parameter with a variable resistor as signal generator and of an appertaining external control device.

Accordingly, a time element 72 is present in the external control circuit. The timer element is started by the transmitter 51 of the external control device with the last signal of the transmission salvo and is stopped by the receiver 53 upon receipt of the acknowledgement signal. The measured time corresponds to the measured value of the pressure/resistance transducer 71 and can be displayed at the display 73. Further, display units 74 and 75 are also present here with which each signal received in the external device, i.e., each motor pulse, is signalized in a known manner or, respectively, the frequency of the signals is measured and displayed. In addition, the encoding circuit 76 with input units 77 and 78 required for the control or, respectively, programming, as well as a separate input 79 to the external drive are indicated. Overall, the control and programming device with receivers and circuits for acknowledgement of the control or, respectively, programming pulses and for detecting an answer back operating parameter for a complete control and monitoring device 100.

Beyond pure signal acknowledgement, thus, an answer back of an operating parameter of the implanted metering device is additionally possible with the circuit arrangement according to FIGS. 5 and 6. However, the coincidence check of the signals and, thus, the acknowledgement of the control and/or programming operation is, so to speak, implicit due to the time measurement in the control and monitoring device. Since all signal transmission operations sequence in the millisecond range, delay times of less than 100 ms are achieved overall in the answer back.

In FIG. 6, the measured value generator should specifically be a pressure/resistance transducer. Such a pressure signal generator for monitoring the pressure in the fluid delivery system was already indicated with reference numeral 29 in the illustration according to FIG. 2. In the simplest case, that can, for example, be a pressure switch which responds when a cut-off value is transgressed; thus, a disruption in the delivery system can already be indicated, wherewith suitable corrective measures can be undertaken.

In the exemplary embodiments of the invention according to FIGS. 4 through 6, the reception coil 41 in the metering device respectively had a separate transmission coil (47 or 46) allocated to it. In addition, in order to expand the external control and/or programming device into a monitoring device, a reception coil (41) was likewise allocated to the transmission coil 50. Of course, it is possible to only provide one respective coil which alternately assumes the reception and transmission function respectively and vice versa. To that end, additional electronic or electromechanical changeover switches are to be provided which respectively switch the coil from the receiver input to the transmitter output and vice versa.

In the description of the exemplary embodiments illustrated we have proceeded from the fact that an entire infusion program is transmitted into the implanted metering device as an encoded signal salvo. With the inventive device and given such metering devices as are designed per se for programming, a direct control of the metering device is also possible while bypassing the deposited program. To that end, signal sequences with the desired frequency are transmitted encoded to the monitoring device 100 with a frequency generator via the external input 79, said signal sequences driving the motor driver with the prescribed frequency proceeding directly from the decoder. In this manner, for example with the assistance of an extra-corporeal glucose sensor and of a suitable control algorithm, a glucose-regulated insulin infusion can be exacted for a specific time, which can be meaningful, particularly in critical patient situations or in order to determine an optimum infusion program.

It will be apparent that many modifications and variations may be effected without departing from the scope of the novel concepts and teachings of the present invention.

SUPPLEMENTARY DICUSSION

In one exemplary transmitter circuit 51 for the illustrated embodiments code signals as represented in the copending application Franetzki and Prestele U.S. Ser. No. 150,180 filed May 15, 1980 (applicant's reference no. VPA 79 P 5035) may be generated for representing a desired infusion program. (Hereafter in this section, reference numerals and figure numbers of Ser. No. 150,180 will be spelled so as to differentiate them from numerals referring to the present drawings.) Thus referring to part B of the fifth figure of Ser. No. 150,180, a pulse sequence may comprise pulses of specified time duration and include a first A pulse train with a first time interval $d_1$ between successive pulses followed by a second B pulse train with a second time interval $d_2$ (e.g. shorter than $d_1$) between the successive pulses. The A pulse salvo may contain a number of A pulses representing a basal infusion rate, and the B pulse salvo may contain a number of B pulses representing a superimposed infusion rate which is to be superimposed on the basal infusion rate for a preestablished time interval, e.g. one hour. The selected A and B pulse trains are supplied by a coder (e.g. as shown at forty-six in the fourth figure of Ser. No. 150,180), to an oscillator (forty-seven) for generating a carrier frequency pulse to represent each pulse of the pulse trains. A suitable driver circuit (forty-eight) may couple the oscillator output with a transmitter coil corresponding to coil 50 herein.

With the foregoing type of transmitter circuit for generating an operational signal transmission in coded form, the reception amplifier 42 herein may comprise an a.c. voltage amplifier, and a pulse amplifier tuned with its lower cut-off frequency to the pulse width of the pulses of the coded signals so as to generate a rectangular pulse in conjunction with a pulse shaper.

The decoder 43 in this case would receive the original A and B pulse trains, and would supply separate outputs to an R line, an A line and a B line. By way of example, the R line would receive a reset pulse in response to a first pulse pair having a time interval $d_1$ so that the initial pulse of this first pulse pair from the encoder of transmitter 51 could be supplied to the monostable circuit 54, FIG. 4 herein, to produce a transmission signal for the evaluation circuitry 55, 56, FIG. 4. Then the reset pulse from the decoder 43, FIG. 4, could generate an acknowledgement pulse at the Q output of the decoder. Where the acknowledgement pulse is utilized to actuate the stepping motor drive, so as to confirm its operational condition, the fact of this further infusion increment, where not completely negligible, can be taken account of in generating a desired program.

Where each coded transmission is to directly produce an infusion increment as in parts A and B of the second figure of Ser. No. 150,180, the acknowledgement pulse is the normal output of the decoder (twenty-five) and can produce the monitoring signal in the external monitor device by its normal operation of the motor drive (twenty-six) and the roller pump (twenty-seven) or by also driving auxiliary answer back components as represented by transmitter coil 47, FIG. 4, which may include a carrier frequency triggered oscillator (such as ten in part A of figure two of Ser. No. 150,180). The receiver such as 53, FIG. 4, may include components such as an a.c. voltage amplifier (twenty-two), a pulse amplifier (such as twenty-three of part A of figure two) and a pulse shaper (twenty-four). In this type of three pulse code, the third pulse as transmitted by the monitor device 3, FIG. 1, may be supplied by the transmitter circuit 51 as a transmission signal whose time relationship to the acknowledgement or answer back signal is to be evaluated by evaluation circuitry such as 53–56, FIG. 4, or 65–59, FIG. 5, or 72–75, FIG. 6. The third pulse from the coder (as shown in part B of figure two) may generate a transmission signal pulse by actuating monostable circuit 54, FIG. 4. Such an actuating pulse for monostable circuit 54 may be generated by circuitry corresponding to that used for the decoder (twenty-five). Figure one of Ser. No. 150,180 specifically indicates the case of an implanted metering device, and may represent any of the metering devices herein.

Where the operational signal transmission to the metering device is in accordance with the seventh figure and parts A and B of the eighth figure of Ser. No. 150,180, the successive values for a twenty-four hour period are sent as a sequence of pulse salvos with specified intervals ($d_1$) therebetween. In this case the last salvo, e.g. number twenty-four where each value is supplied for one hour, can generate the transmission signal with its initial pulse, such initial pulse producing an address pulse for advancing the address counter (seventy-eight). Simply as a concrete example, the Q output of decoder 43, FIG. 5, can be generated with the use of an address-counter-controlled decoder circuit associated with the address counter (seventy-eight) so that a pulse is generated when the address counter is set to an address number twenty-four. Of course, such coordination of the generation of a transmission signal (e.g. a start signal for counter 66, FIG. 5) with the generation of an acknowledgement or answer back signal at the decoder (e.g. decoder 43, FIG. 5) is a matter of routine for one of ordinary skill in the art.

In each of the embodiments herein, the metering device may be implanted as shown in Ser. No. 150,180, and may be controlled by any one of the external coding units of Ser. No. 150,180. The external monitor device may be separate from the coding unit, and may be provided with a receiving coil such as 31, FIG. 3, and reception circuitry and decoder circuitry with Q output (such as also used in the implanted metering device which is also to receive the coded signal transmission) for generating the transmission signal simultaneously with generation of the acknowledgement or answer back signal at the corresponding decoder of the implanted metering device.

Referring to FIG. 4, a carrier frequency generating means may be interposed between the motor driver 45 and transmitter coil 47 for generating a carrier frequency pulse signal in response to each operation of the motor driver 45. Such carrier frequency generator may be considered to be part of component 47 for a modified embodiment in accordance with FIG. 4.

Referring to FIG. 6, for example, the motor driven 45 may include a counter circuit for summing the number of actuations of the stepping motor 46. In this case variable resistance 71 may be formed by a digital to analog circuit controlled by the count value of the counter circuit to present a corresponding resistance value (as the value of resistance 71). Thus the response circuit from decoder 43 which includes variable time delay 70 supplies a response signal to the motor driver 45 which is delayed in accordance with the attained count value of the actuation counting circuit associated with the motor driver 45. The timer circuit 72 then interprets the delayed response signal as received by coil 52 in relation to the start or transmission signal from circuit 51 as representing the number of actuations of the motor driver 45 either over the operating life of the implanted metering unit or as the number of actuations since a previous readout (where the counter circuit is reset by the delayed response signal from time delay 70 via a separate line from the output of 70 to a reset circuit, not shown).

We claim as our invention:

1. An infusion system for the infusion of fluids into the human or animal body, said system comprising
   (a) a metering device to be implanted within the body, having a delivery unit for the dosed delivery of fluid to the body, said delivery unit having operating circuitry for controlling operation of the delivery unit, and said metering device having coupling means for receiving an operational signal transmission and for effecting an operation in accordance therewith,
   (b) an external monitor device having coupling means coupled with said metering device for supplying a monitoring signal in accordance with an operation produced at the metering device by an operational signal transmission, and
   (c) evaluation means operatively associated with said external monitor device for receiving a transmission signal in accordance with an operational signal transmission transmitted to the metering device, and connected with the coupling means of the external monitor device for receiving a monitoring signal in accordance with an operation at the metering device produced by an operational signal transmission, and operative for supplying an information signal where a received monitoring signal has a predetermined relationship to a received transmission signal, the information signal thereby being indicative of receipt of the operational signal transmission by the metering device,
   (d) the delivery unit comprising a roller pump and a stepping motor drive therefor, said coupling means of said metering device comprising an induction coil associated with the roller pump for coupling with the coupling means of the external monitor device, said induction coil being connected with the stepping motor drive and said stepping motor drive being actuated by an operational signal transmission so as to cause the coupling means of the external control device to supply said monitoring signal in a predetermined relationship to the operational signal transmission, and
   (e) said evaluation means comprising time sensitive comparison means for receiving the transmission signal to initiate a timing comparison and receiving the monitoring signal upon actuation of the stepping motor drive by the operational signal transmission, and being operative to compare the timing relationship between said transmission signal and said monitoring signal and supplying said information signal only where a received monitoring signal has a predetermined timing relationship to a received transmission signal, said time sensitive comparison means thereby being operative to monitor for an answer back response resulting directly from an actual test operation of said stepping motor drive, as well as to discriminate such answer back response from incorrectly timed spurious signals.

2. An infusion system according to claim 1, with said coupling means of said metering device comprising a separate induction coil (47) for actuation by an operational signal transmission so as to cause the coupling means of the external monitor device to supply said monitoring signal in a predetermined relationship to the operational signal transmission.

3. An infusion system according to claim 3, with said coupling means of the metering unit comprising carrier frequency generator means for actuation by an operational signal transmission to generate a carrier frequency signal for coupling with the coupling means of the external monitor device.

4. An infusion system according to claim 1, with said external monitor device having transmitter means connected with said evaluation means and operable to transmit an operational signal transmission to said metering unit and to send a transmission signal to the evaluation means which has a predetermined time relationship to said operational signal transmission.

5. An infusion system according to claim 4, with said time sensitive comparison means having logic means for generating an information signal only when the transmission signal and the monitoring signal both occur within a predetermined time interval.

6. An infusion system according to claim 1, with said external monitor device having an induction coil for coupling with the coupling means of the metering unit, and having a transmitter circuit connected with said induction coil of the external monitor device for actuating the same to produce transmission of an operational signal transmission, said transmitter circuit being connected to said evaluation means for sending a transmission signal thereto which has a predetermined time relationship to said operational signal transmission.

7. An infusion system for the infusion of fluids into the human or animal body, said system comprising
   (a) a metering device to be implanted within the body, having a delivery unit for the dosed delivery of fluid to the body, said delivery unit having operating circuitry for controlling operation of the delivery unit, and said metering device having coupling means for receiving an operational signal transmission and for effecting an operation in accordance therewith,
   (b) an external monitor device having coupling means coupled with said metering device for supplying a monitoring signal in accordance with an operation produced at the metering device by an operational signal transmission, and
   (c) evaluation means operatively associated with said external monitor device for receiving a transmission signal in accordance with an operational signal transmission transmitted to the metering device, and connected with the coupling means of the external monitor device for receiving a monitoring signal in accordance with an operation at the metering device produced by an operational signal transmission, and operative for supplying an information signal where a received monitoring signal has a predetermined relationship to a received transmission signal, the information signal thereby being indicative of receipt of the operational signal transmission by the metering device,
   (d) said coupling means of said metering device comprising a receiver induction coil connected with the delivery unit for actuating said delivery unit upon receipt of an operational signal transmission, and said coupling means of said external monitor device comprising a receiver induction coil for supplying the monitoring signal in response to actuation of the delivery unit,
   (e) said evaluation means being connected to the receiver induction coil of the monitor device so as to supply said information signal only when the operational signal transmission actually causes actuation of the delivery unit and the resultant monitoring signal from the receiver induction coil of the monitor device has the predetermined relationship to the transmission signal.

8. An infusion system according to claim 1, with said monitor device including control circuitry for generating an operational signal transmission representing a control signal for the operating circuitry of said metering device.

9. An infusion system according to claim 8, with said coupling means of the external monitor device comprising transmission means (51) for generating a control signal for the operating circuitry of the metering device, and a monostable circuit (54) connected with said transmission means and operable for supplying said transmission signal for a predetermined time interval, said evaluation means comprising a logical circuit (55) connected with said monostable circuit (54) and operable for generating the information signal in response to the time coincidence of the monitoring signal with said transmission signal.

10. An infusion system according to claim 1, with said monitor device including control cicuitry for generating an operational signal transmission representing a control signal for the operating circuitry of said metering device, said control circuitry comprising an encoder for generating an operational signal transmission in the form of an encoded control signal, said operating circuitry of said metering device including a decoder connected with the coupling means of the metering device and operative in response to said encoded control signal to effect an operation of the metering device which generates an acknowledgement signal and causes the coupling means of the external monitor device to supply said monitoring signal.

11. An infusion system according to claim 10, with said operating circuitry of the metering device having memory means connected with said decoder for storing an infusion program in accordance with an encoded control signal, and said coupling means of said metering device comprising a transmission coil for transmitting an acknowledgement signal and response circuit means connecting said decoder with said transmission coil and bypassing said memory means for producing an acknowledgement signal occurring within a predetermined time interval after decoding of an encoded control signal by said decoder.

12. An infusion system according to claim 10, with said elevation means comprising a logical circuit (55) for generating the information signal in dependence on the time coincidence of the transmission signal and the monitoring signal.

13. An infusion system according to claim 12 with said evaluation means having a display unit (56) connected with said logical circuit (55) and being actuated by the information signal to indicate that the operational signal transmission has been received by the metering unit.

14. An infusion system for the infusion of fluids into the human or animal body, said system comprising
 (a) a metering device to be implanted within the body, having a delivery unit for the dosed delivery of fluid to the body, said delivery unit having operating circuitry for controlling operation of the delivery unit, and said metering device having coupling means for receiving an operational signal transmission and for effecting an operation in accordance therewith,
 (b) an external monitor device having coupling means coupled with said metering device for supplying a monitoring signal in accordance with an operation produced at the metering device by an operational signal transmission, and
 (c) evaluation means operatively associated with said external monitor device for receiving a transmission signal in accordance with an operational signal transmission transmitted to the metering device, and connected with the coupling means of the external monitor device for receiving a monitoring signal in accordance with an operation at the metering device produced by an operational signal transmission, and operative for supplying an information signal where a received monitoring signal has a predetermined relationship to a received transmission signal, the information signal thereby being indicative of receipt of the operational signal transmission by the metering device,
 (d) said metering device having a response circuit connected with said coupling means and providing for operation of the metering device so as to supply an acknowledgement signal occurring within a specific time interval relative to a received operational signal transmission.

15. An infusion system according to claim 14, with said metering device having sensing means for sensing a parameter of the metering device, and said response circuit being controlled by said sensing means for transmitting a response signal upon receipt by the metering device of an operational signal transmission, said response circuit operating to provide a time interval between receipt of the operational signal transmission and transmission of said response signal which is determined by the condition of said parameter.

16. An infusion system according to claim 15, with said sensing means comprising a pressure-resistance transducer for sensing a pressure value of the metering device.

17. An infusion system according to claim 14, with said metering device sensing a plurality of parameters and providing said response circuit for operation in response to an operational signal transmission so as to automatically supply a series of response signals with time intervals between successive response signals being functions of the respective parameters.

18. An infusion system according to claim 17, with said evaluation means of said monitor device comprising a counter for beginning a counting cycle in response to said transmission signal, and storage means responsive to monitoring signals produced by successive response signals from the metering unit to register successive count values in accordance with the respective parameters of the metering unit.

19. An infusion system according to claim 18, with said storage means comprising a register stack having a predetermined sequence of storage positions and responsive to successive monitoring signals to store successive count values attained by said counter at successive ones of said predetermined sequence of storage positions such that the location of each stored count value in said register stack identifies the parameter represented thereby.

20. An infusion system according to claim 14, with said metering device having a measured value generator for sensing a parameter thereof, said response circuit comprising at least one controllable time delay element controlled by said measured value generator, said metering device being responsive to an operational signal transmission to supply successive signals with a time interval therebetween under the control of said time delay element.

21. An infusion system according to claim 20, with said measured value generator comprising a pressure-resistance transducer providing a resistance value in accordance with a pressure of the metering device, and said controllable time delay element comprising a monostable circuit having a delay interval in accordance with the resistance value of said pressure-resistance transducer.

22. An infusion system according to claim 14, with said metering device having a plurality of measured value generators for measuring respective parameters of the metering device, said response circuit comprising respective controllable time delay elements connected in series and controlled by the respective measured value generators, said time delay elements being responsive to an operational signal transmission to supply a succession of response signals having time intervals in accordance with the successive time delay elements.

23. An infusion system according to claim 14, with said response circuit being responsive to an operational signal transmission to supply an acknowledgement signal having a characteristic in accordance with an internal pressure of the metering device, said evaluation means of said monitor device having means for registering the value of such pressure as transmitted thereto by means of the acknowledgement signal.

24. An infusion system according to claim 14, with said response circuit being responsive to an operational signal transmission to supply an acknowledgement signal having a characteristic in accordance with a pressure at which fluid is supplied from the delivery unit, said evaluation means of said monitor device having means for registering the value of such pressure as transmitted thereto by means of the acknowledgement signal.

25. An infusion device according to claim 14, with said metering device having a counter for summing the number of actuations of the delivery unit, and said response circuit being responsive to an operational signal transmission to supply a response signal having a characteristic which is a function of the count condition of said counter, said evaluation means of said monitor device being controlled by said response signal for registering said count condition.

26. An infusion system according to claim 14, with said evaluation means comprising a timer responsive to said transmission signal to begin a timing operation, and responsive to a monitoring signal to stop said timing operation.

27. An infusion system according to claim 26, with said timer comprising a counter and a clock generator for supplying counting pulses to said counter during a counting cycle, said evaluation means starting a counting cycle of the counter in response to said transmission signal and stopping the counting cycle in response to a monitoring signal.

28. An infusion system according to claim 3, with the delivery unit comprising a roller pump and a stepping motor drive therefor, said response circuit bypassing said operating circuitry and being operative for actuating said stepping motor drive in response to an operational signal transmission, said coupling means of said external monitor device being responsive to actuation of said stepping motor drive to supply said monitoring signal.

* * * * *